United States Patent [19]
Almond

[11] Patent Number: 6,016,915
[45] Date of Patent: Jan. 25, 2000

[54] SINGLE-USE FIRST AID KIT

[76] Inventor: John D. Almond, 5907 5th Ct., Northport, Ala. 35476

[21] Appl. No.: 09/304,394

[22] Filed: May 4, 1999

[51] Int. Cl.$^7$ .................................................. B65D 75/28
[52] U.S. Cl. ........................................... 206/570; 206/441
[58] Field of Search ..................................... 206/209, 210, 206/229, 438, 440, 441, 570–572

[56] References Cited

U.S. PATENT DOCUMENTS

| | | |
|---|---|---|
| 779,266 | 1/1905 | Davis . |
| 1,129,485 | 2/1915 | Harman . |
| 1,234,397 | 7/1917 | Schultz ..................................... 206/570 |
| 2,108,492 | 2/1938 | Lagier . |
| 2,804,969 | 9/1957 | Barnett . |
| 3,013,656 | 12/1961 | Murphy, Jr. .............................. 206/572 |
| 4,696,393 | 9/1987 | Laipply ..................................... 206/441 |
| 4,915,228 | 4/1990 | Johns ....................................... 206/441 |
| 5,117,981 | 6/1992 | Crawford ................................. 206/570 |
| 5,178,282 | 1/1993 | Williams .................................. 206/570 |
| 5,718,245 | 2/1998 | Horn . |
| 5,931,304 | 8/1999 | Hammond ................................ 206/570 |

*Primary Examiner*—Jim Foster
*Attorney, Agent, or Firm*—Kenneth M. Bush; Veal & Bush, LLC

[57] ABSTRACT

A single-use first aid kit having at least one antiseptic wipe to clean a minor wound, an antibiotic ointment to medicate the wound, and at least one bandage to cover the wound. The kit is substantially planar and lightweight so that it can be conveniently carried on an individual.

21 Claims, 5 Drawing Sheets

SINGLE-USE FIRST AID KIT

FIELD OF THE INVENTION

The present invention relates to first aid kits. More particularly, the present invention relates to a single-use first aid kit for cleaning, medicating, and covering a minor wound, wherein the kit is compact and lightweight so that it can be conveniently carried on an individual.

BACKGROUND OF THE INVENTION

First aid kits having the supplies necessary for treating a variety of minor injuries are known in the art. A feature of most first aid kits is their substantial weight and bulkiness due to the quantity and type of supplies included therein. Because of this feature, first aid kits are generally stored in homes, vehicles, and the like, rather than constantly carried by individuals. As a result, many minor injuries occur in locations where a first aid kit is not immediately available.

While first aid kits have been developed which are "pocket-sized" so that they can be carried on an individual, these kits are still too bulky to be comfortably carried within an individual's shirt or pants pocket, and cannot be carried in an individual's wallet at all. As a result, present pocket-sized first aid kits are generally only carried by individuals who routinely encounter situations where immediate first aid is required. Since minor wounds should be treated as soon as possible to prevent infection, what is needed is a compact and lightweight first aid kit which overcomes the problems found with prior art "pocket-sized" first aid kits so that individuals will not be reluctant to carry the kit.

SUMMARY OF THE PRESENT INVENTION

It is an object of the present invention to provide a single-use first aid kit which contains the minimal items required to clean, medicate, and cover a minor wound.

It is another object of the present invention to provide a first aid kit which is compact and lightweight so that it can be conveniently carried on an individual.

It is another object of the present invention to provide a first aid kit which is substantially planar so that it can be conveniently carried in a pocket, wallet, billfold, purse, bag, etc.

These and other objects of the present invention are accomplished with a single-use first aid kit having at least one antiseptic wipe to clean a minor wound, an antibiotic ointment to medicate the wound, and at least one bandage to cover the wound. The kit is substantially planar and lightweight so that it can be conveniently carried on an individual.

These and other objects and advantages of the invention will become apparent from the following detailed description of the preferred embodiment of the invention.

BRIEF DESCRIPTION OF THE DRAWINGS

A first aid kit embodying features of the invention is described in the accompanying drawings which form a portion of this disclosure and wherein.

DETAILED DESCRIPTION OF THE PREFERRED EMBODIMENT

Figure 1:
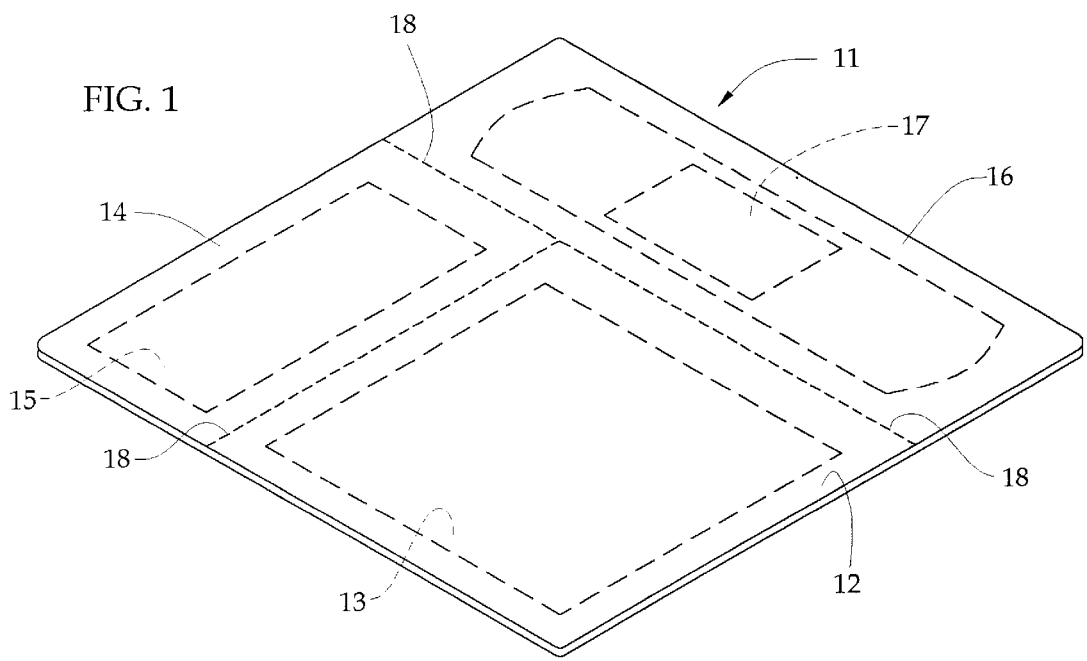
FIG. 1 is a perspective view of the present invention.

A more complete understanding of the invention may be obtained by reference to the accompanying drawings wherein the invention is a sterile, single-use first aid kit 11 for treating a minor wound wherein the preferred embodiment comprises at least 3 compartments in a side-by-side relationship as shown in FIGS. 1–4, wherein a first compartment 12 comprises at least one antiseptic wipe or towelette 13 for cleaning the wound, a second compartment 14 comprises an antibiotic ointment 15 for medicating the wound, and a third compartment 16 comprises at least one adhesive bandage 17 for covering the wound. In an alternate embodiment shown in FIG. 5, the kit can have the antiseptic and antibiotic-containing compartments 12, 14 superimposed over the bandage-containing compartment 16. The particular antiseptic and antibiotic agents are selected from those commonly known and available in the medical industry and will not be set forth herein. Moreover, alternate cleaning and medicating agents known in the medical industry could be substituted for the antiseptic and antibiotic agents, respectively, and other agents, such as anesthetics, can be included with the cleaning and/or medicating agents.

Figure 2:
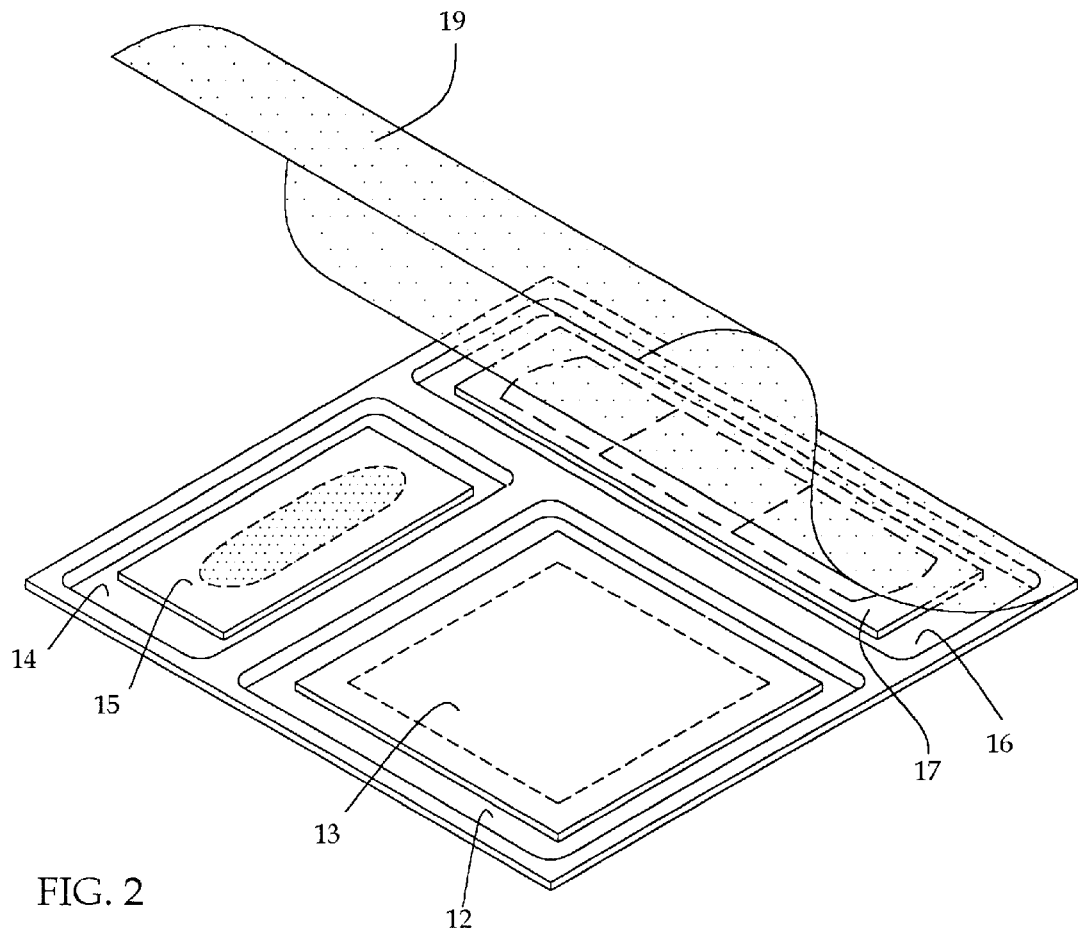
FIG. 2 is a perspective view of an alternate embodiment of the present invention.
Figure 3:
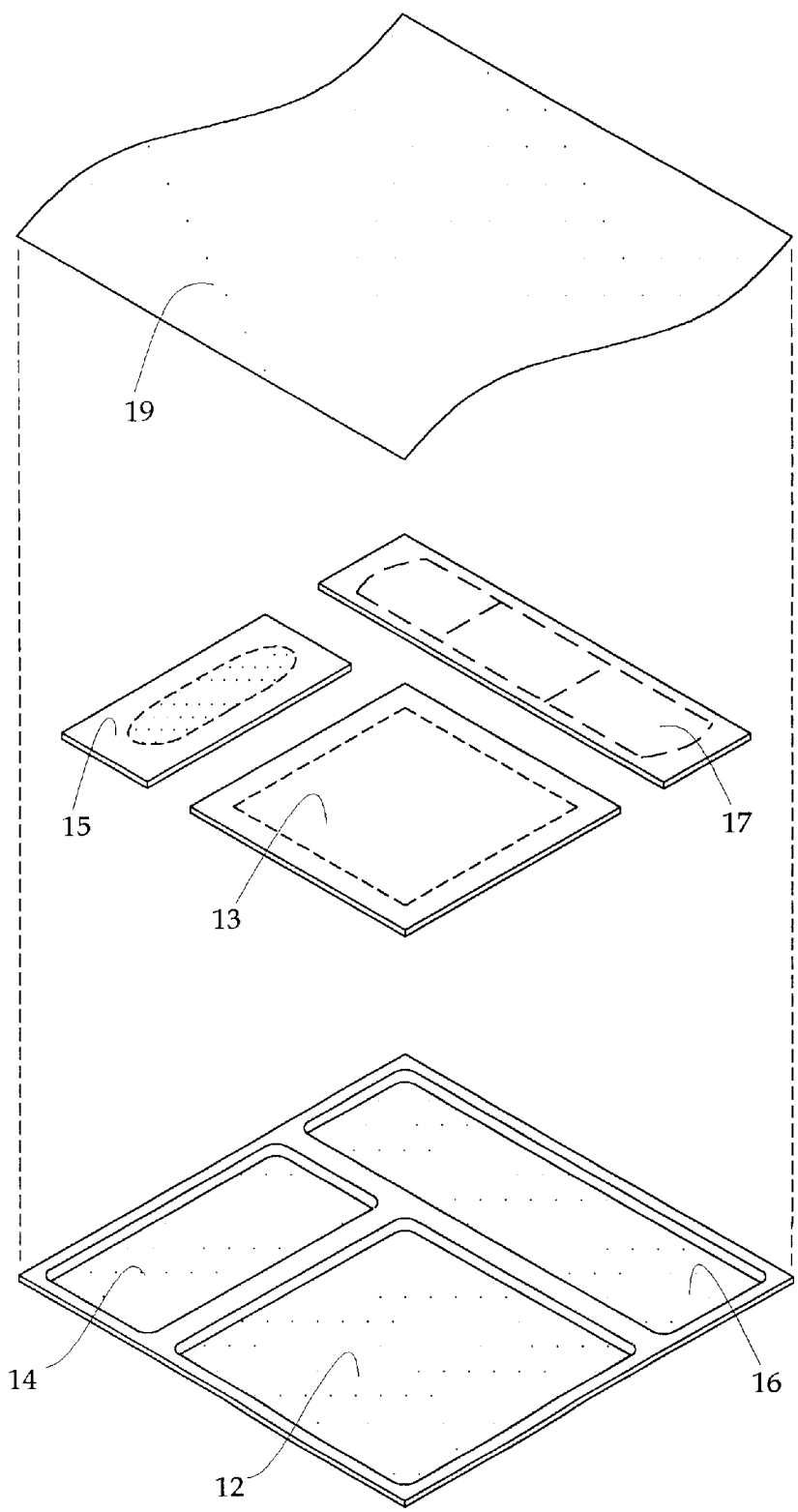
FIG. 3 is an exploded perspective view of the embodiment of FIG. 2.
Figure 4:
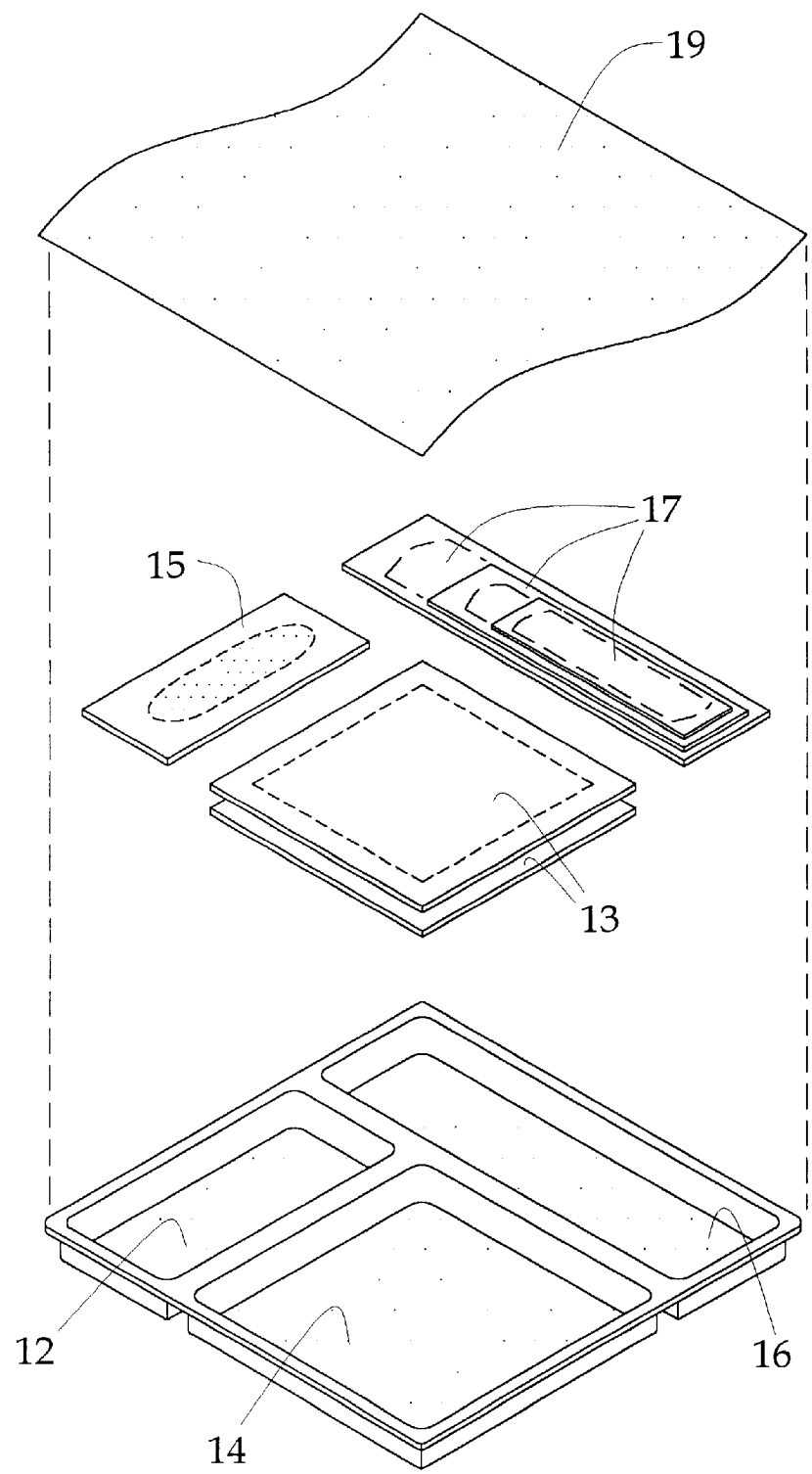
FIG. 4 is an exploded perspective view of an alternate embodiment of the present invention.
Figure 5:
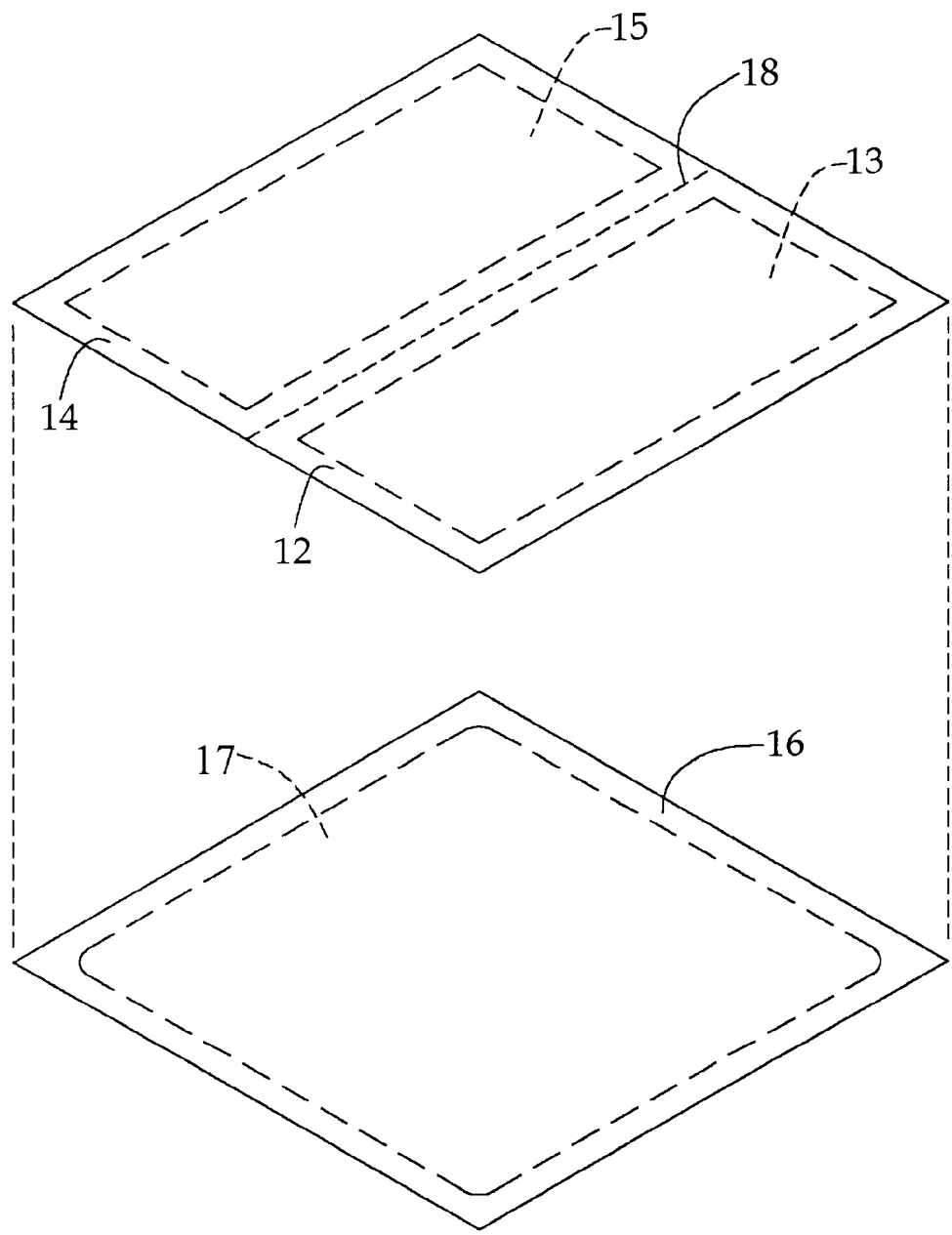
FIG. 5 is an exploded perspective view of an alternate embodiment of the present invention.

The kit 11 is preferably comprised of a waterproof, flexible material such as a wax or plastic coated paper, plastic, or metal foil, or other suitable packaging material as is known in the packaging industry. The compartments 12, 14, 16 are preferably individually hermetically sealed and can be separated by perforations 18 such that the individual compartments may be easily separated from one another for use, as shown in FIGS. 1 and 5, or alternatively, the items 13, 15, 17 may be individually packaged and placed within their respective compartments and sealed with a peelable cover 19, preferably comprising a transparent plastic film or foil, as shown in FIGS. 2–4. Further, the kit can include a plurality of each item, as shown in FIG. 4.

Unlike prior art "pocket-sized" first aid kits, the kit of the present invention is substantially planar and lightweight so that it can be comfortably carried on an individual, such as in their shirt or pants pocket or in their wallet or billfold. The kit is preferably less than one-fourth inch in thickness, and most preferably less than one-eighth inch in thickness. The kit is preferably less than 5 inches in length and less than 4 inches in width, and most preferably less than 4 inches in length and less than 3 inches in width. The kit is preferably less than 2 ounces in weight, and most preferably less than 0.5 ounce in weight. The kit can be rigid or flexible, although the flexible embodiment is preferred because it can be comfortably carried in an individual's pants pocket, wallet, or billfold.

It is to be understood that the form of the invention shown is a preferred embodiment thereof and that various changes and modifications may be made therein without departing from the spirit of the invention or scope as defined in the following claims.

Having set forth the nature of the invention, what is claimed is:

1. A single-use first aid kit for treating a minor wound, comprising at least one antiseptic wipe for cleaning the wound, an antibiotic ointment for medicating the wound, and at least one bandage for covering the wound, wherein the kit is substantially planar.

2. A kit according to claim 1, wherein the kit is less than one-fourth inch in thickness.

3. A kit according to claim 1, wherein the kit is less than one-eighth inch in thickness.

4. A kit according to claim 1, wherein the kit is less than 5 inches in length and less than 4 inches in width.

5. A kit according to claim 1, wherein the kit is less than 4 inches in length and less than 3 inches in width.

6. A kit according to claim 1, wherein the kit is between 3 to 5 inches in length and between 2 to 4 inches in width.

7. A kit according to claim 1, wherein the kit is less than 2 ounces in weight.

8. A kit according to claim 1, wherein the kit is less than 0.5 ounce in weight.

9. A first aid kit, comprising at least three hermetically sealed compartments, wherein a first compartment comprises a cleaning agent, a second compartment comprises a medicating agent, and a third compartment comprises at least one adhesive bandage.

10. A kit according to claim 9, wherein said cleaning agent comprises at least one antiseptic wipe.

11. A kit according to claim 9, wherein said medicating agent comprises an antibiotic ointment.

12. A kit according to claim 9, wherein the kit is substantially planar.

13. A kit according to claim 12, wherein the kit is less than one-fourth inch in thickness.

14. A kit according to claim 12, wherein the kit is less than one-eighth inch in thickness.

15. A kit according to claim 9, wherein the kit is less than 2 ounces in weight.

16. A kit according to claim 9, wherein the kit is less than 0.5 ounce in weight.

17. A kit according to claim 9, wherein said hermetically sealed compartments are separated from one another by perforations in the kit such that said compartments may be easily detached from one another.

18. A kit according to claim 9, wherein the kit is flexible.

19. A first aid kit for treating a minor wound, comprising at least three hermetically sealed compartments in a side-by-side relationship, wherein a first compartment comprises means for cleaning the wound, a second compartment comprises means for medicating the wound, and a third compartment comprises means for covering the wound, and wherein the kit is substantially planar.

20. A kit according to claim 19, wherein the kit is less than one-eighth inch in thickness.

21. A kit according to claim 19, wherein the kit is less than 0.5 ounce in weight.

* * * * *